(12) United States Patent
Chen et al.

(10) Patent No.: US 11,939,603 B1
(45) Date of Patent: Mar. 26, 2024

(54) CUTINASE HAVING IMPROVED ENZYMATIC ACTIVITY

(71) Applicant: Hubei University, Wuhan (CN)

(72) Inventors: Chun-Chi Chen, Wuhan (CN); Jian-Wen Huang, Wuhan (CN); Jian Min, Wuhan (CN); Xian Li, Wuhan (CN); Beilei Shi, Wuhan (CN); Panpan Shen, Wuhan (CN); Yu Yang, Wuhan (CN); Yumei Hu, Wuhan (CN); Longhai Dai, Wuhan (CN); Lilan Zhang, Wuhan (CN); Yunyun Yang, Wuhan (CN); Rey-Ting Guo, Wuhan (CN)

(73) Assignee: HUBEI UNIVERSITY, Wuhan (CN)

( * ) Notice: Subject to any disclaimer, the term of this patent is extended or adjusted under 35 U.S.C. 154(b) by 0 days.

(21) Appl. No.: 18/339,218

(22) Filed: Jun. 21, 2023

(30) Foreign Application Priority Data

Feb. 8, 2023 (CN) .......................... 202310105886.5

(51) Int. Cl.
*C12N 9/18* (2006.01)

(52) U.S. Cl.
CPC ........ *C12N 9/18* (2013.01); *C12Y 301/01074* (2013.01)

(58) Field of Classification Search
CPC ......................... C12N 9/18; C12Y 301/01074
See application file for complete search history.

(56) References Cited

PUBLICATIONS

NCBI Caldimonas taiwanesis protein accession (https://www.ncbi.nlm.nih.gov/protein/WP_062195544.1) (Year: 2023).*

* cited by examiner

*Primary Examiner* — Walter E Webb
*Assistant Examiner* — Rachel Emily Martin
(74) *Attorney, Agent, or Firm* — KIRTON McCONKIE; Evan R. Witt

(57) ABSTRACT

A modified cutinase is disclosed. The cutinase has the modified amino acid sequence of SEQ ID NO: 2, wherein the modification is a substitution of asparagine at position 181 with alanine, or substitutions of asparagine at position 181 with alanine and phenylalanine at position 235 with leucine. The modified enzyme has improved PET-hydrolytic activity, and thus, the high-activity PET hydrolase is obtained, and the industrial application value of the PET hydrolase is enhanced.

5 Claims, 7 Drawing Sheets

Specification includes a Sequence Listing.

```
agcccatcgaccctctcaacaatcctgctggccgactgcgccgcgctggccgcaccgggcctggccaggcgaacccatatcaaaaaggc
 S  P  S  T  L  S  T  I  L  A  A  C  A  L  A  A  P  G  L  A  Q  A  N  P  Y  Q  K  G ccgatcccacggcttcggccttggaacgcaacgggccgtttgccatccgcagcaactcggtgtcgcgcacctcggtcagcggcttcggc
 P  D  P  T  A  S  A  L  E  R  N  G  F  F  A  I  R  S  T  S  V  S  R  T  S  V  S  G  F  G ggcggacgcctgtactatccgaccgccagcggcacctacggcgccatcgcggtgtcgccgggttcaccggcacgtcctcgaccatgacc
 G  G  R  L  Y  Y  P  T  A  S  G  T  Y  G  A  I  A  V  S  P  G  F  T  G  T  S  S  T  M  T ttctggggcgagcgcctggcttcgcacggcttcgtcgtgctggtgatcgacaccatcaccttgtacgaccagccgacagccgcgccgt
 F  W  G  E  R  L  A  S  H  G  F  V  V  L  V  I  D  T  I  T  L  Y  D  Q  P  D  S  R  A  R cagctcaaggcagcactggactacctggccacgcagaacggccgcagcagcccgatctacgcaaggtcgacaccagccgcgcgcc
 Q  L  K  A  A  L  D  Y  L  A  T  Q  N  G  R  S  S  P  I  Y  R  K  V  D  T  S  R  A gtggccggccattcgatgggcggaggcggctcgctgctggccgcgcgtgacaatccagttacaaagccgccatcccgatggcaccctgg
 V  A  G  H  S  M  G  G  G  S  L  L  A  A  R  D  N  P  S  Y  K  A  A  I  P  M  A  P  W aacacctcgtccacggccttccgcacggtcagcgtgcccacgatgatcttcggctgtcaggacgacagcatcgcccggtgttcagctct
 N  T  S  S  T  A  F  R  T  V  S  V  P  T  M  I  F  G  C  Q  D  D  S  I  A  P  V  F  S  S gcgatcccgatttacaacgccattccaacagcacgcgcaagaactatgtcgagatccgcaatgacgaccacttctgcgtgatgaacggc
 A  I  P  I  Y  N  A  I  P  N  S  T  R  K  N  Y  V  E  I  R  N  D  D  H  F  C  V  M  N  G ggtgggcatgatgccacgctgggcaagctgggcatctcgtggatgaagcgcttcgtcgacaacgacacgcgctacagcccttcgtctgc
 G  G  H  D  A  T  L  G  K  L  G  I  S  W  M  K  R  F  V  D  N  D  T  R  Y  S  P  F  V  C ggtgcggaatacaaccgcgtggtcagcagctacgaggtctcgcgttcgtacaacaactgtccgtac        - SEQ ID NO. 1
 G  A  E  Y  N  R  V  V  S  S  Y  E  V  S  R  S  Y  N  N  C  P  Y               - SEQ ID NO. 2
``` agcccatcgaccctctcaacaatcctgctggccgcctgcgccgcgctggccgcaccgggcctggcccaggcgaacccatatcaaaaggc
S P S T L S I L L A A C A A L A A P G L A Q A N P Y Q K G cccgatccacggcttcggccttggaacgcaacgggccgtttgccatccgcagcacctcggtgtcgcgcacctcggtcagcggcttcggc
P D P T A S A L E R N G F F A I R S T S V S R T S V S G F G ggcggacgcctgtactatccgaccgccagcggcacctacggcgccatcgcggtgtcgccgggttcaccggcacgtcctcgaccatgacc
G G R L Y Y P T A S G T Y G A I A V S P G F T G T S S T M T ttctggggcgagcgcctggcttcgcacggcttcgtcgtgctggtgatcgacaccatcaccttgtacgaccagcccgacagccgcgcccgt
F W G E R L A S H G F V V L V I D T I T L Y D Q P D S R A R cagctcaaggcagcactggactacctggccacgcagaacggccgcagcagcagcccgatctaccgcaaggtcgacaccagccgccgcgcc
Q L K A A L D Y L A T Q N G R S S S P I Y R K V D T S R R A gtggccggccattcgatgggcggaggcggctcgctgctggccgcgcgtgacaatccagttacaaagccgccatcccgatggcaccctgg
V A G H S M G G G G S L L A A R D N P S Y K A A I P M A P W aacacctcgtccacggccttccgcacggtcagcgtgcccacgatgatcttcggctgtcaggacgacagcatcgccccggtgttcagctct
N T S S T A F R T V S V P T M I F G C Q D D S I A P V F S S gcgatcccgatttacaacgccattcccaacagcacgcgcaagaactatgtcgagatccgcaatgacgaccacttctgcgtgatgaacggc
A I P I Y N A I P N S T R K N Y V E I R N D D H F C V M N G ggtgggcatgatgccacgctgggcaagctgggcatctcgtggatgaagcgcttcgtcgacaacgacacgcgctacagcccttcgtctgc
G G H D A T L G K L G I S W M K R F V D N D T R Y S P P V C ggtgcggaatacaaccgcgtggtcagcagctacgaggtctcgcgttcgtacaacaactgtccgtac  - SEQ ID NO. 1
G A E Y N R V V S S Y E V S R S Y N N C P Y  - SEQ ID NO. 2

FIG. 1

| Mutant | Primer Sequence (5'→3') |
|--------|--------------------------|
| N181A | CCCGATGGCACCCTGGGCAACCTCGTCCACGGCCTTCCGC (SEQ ID NO. 3) |
| F235L | CCGCAATGACGACCACTTATGCGTGATGAACGGC (SEQ ID NO. 4) |

FIG. 2 agcccatcgaccctctcaacaatcctgctggccgcctgcgccgcgctggccgcaccgggcctggcccaggcgaacccatatcaaaaggc
 S  P  S  T  L  S  T  I  L  L  A  A  C  A  A  L  A  A  P  G  L  A  Q  A  N  P  Y  Q  K  G ccgatccacggcttcggccttggaacgcaacgggccgtttgccatccgcagcacctcggtgtcgcgcacctcggtcagcggcttcggc
 P  D  P  T  A  S  A  L  E  R  N  G  P  F  A  I  R  S  T  S  V  S  R  T  S  V  S  G  F  G ggcggacgcctgtactatccgaccgcagcggcacctacggcgccatcgcggtgtcgccgggttcaccggcacgtcctcgaccatgacc
 G  G  R  L  Y  Y  P  T  A  S  G  T  Y  G  A  I  A  V  S  P  G  F  T  G  T  S  S  T  M  T ttctggggcgagcgcctggcttcgcacggcttcgtcgtgctggtgatcgacaccatcaccttgtacgaccagcccgacagccgcgcccgt
 F  W  G  E  R  L  A  S  H  G  F  V  V  L  V  I  D  T  I  T  L  Y  D  Q  P  D  S  R  A  R cagctcaaggcagcactggactacctggccacgcagaacggccgcagcagcagcccgatctaccgcaaggtcgacaccagccgccgcgcc
 Q  L  K  A  A  L  D  Y  L  A  T  Q  N  G  R  S  S  S  P  I  Y  R  K  V  D  T  S  R  R  A gtggccggccattcgatgggcggaggcggctcgctgctggccgcgcgtgacaatccagttacaaagccgccatcccgatggcaccctgg
 V  A  G  H  S  M  G  G  G  G  S  L  L  A  A  R  D  N  P  S  Y  K  A  A  I  P  M  A  P  W gcaacctcgtccacggccttcgcaacggtcagcgtgcccacgatgatcttcggctgtcaggacgacagcatcgcccgtgttcagctct
 A  T  S  S  T  A  F  R  T  V  S  V  P  T  M  I  F  G  C  Q  D  D  S  I  A  P  V  F  S  S gcgatcccgatttacaacgccattcccaacagcacgcgcaagaactatgtcgagatccgcaatgacgaccacttctgcgtgatgaacggc
 A  I  P  I  Y  N  A  I  P  N  S  T  R  K  N  Y  V  E  I  R  N  D  D  H  F  C  V  M  N  G ggtgggcatgatgccacgctgggcaagctgggcatctcgtggatgaagcgcttcgtcgacaacgacacgcgctacagcccttcgtctgc
 G  G  H  D  A  T  L  G  K  L  G  I  S  W  M  K  R  F  V  D  N  D  T  R  Y  S  P  F  V  C ggtgcggaatacaaccgcgtggtcagcagctacgaggtctcgcgttcgtacaacaactgtccgtac      - SEQ ID NO. 5
 G  A  E  Y  N  R  V  V  S  S  Y  E  V  S  R  S  Y  N  N  C  P  Y          - SEQ ID NO. 6

FIG. 3

```
agccatcgaccctctcaacaatcctgctggccgcctgcgccgcgctggccgcaccgggcctggcccaggcgaacccatatcaaaaggc
 S  P  S  T  L  S  I  L  L  A  A  C  A  A  L  A  A  P  G  L  A  Q  A  N  P  Y  Q  K  G ccgatccacggcttcggccttggaacgcaacgggccgtttgccatccgcagcacctcggtgtcgcgcacctcggtcagcggcttcggc
 P  D  P  T  A  S  A  L  E  R  N  G  P  F  A  I  R  S  T  S  V  S  R  T  S  V  S  G  F  G ggcggacgcctgtactatccgaccgccagcggcaccatacggcgccatcgcggtgtcgccggggttcaccggcacgtcctcgaccatgacc
 G  G  R  L  Y  Y  P  T  A  S  G  T  Y  G  A  I  A  V  S  P  G  F  T  G  T  S  S  T  M  T ttctggggcgagcgcctggcttcgcacggcttcgtcgtgctggtgatcgacaccatcaccttgtacgaccagccgacagccgcgcccgt
 F  W  G  E  R  L  A  S  R  G  F  V  V  L  V  I  D  T  I  T  L  Y  D  Q  P  D  S  R  A cagctcaaggcagcactggactacctggccacgcagaacggccgcagcagcccgatctaccgcaaggtcgacaccagccgccgcgcc
 Q  L  K  A  A  L  D  Y  L  A  T  Q  N  G  R  S  S  P  I  Y  R  K  V  D  T  S  R  R  A gtggccggccattcgatggcggaggcggctcgctgctggccgcgcgtgacaatccagttacaaagccgccatccgatggcaccctgg
 V  A  G  H  S  M  G  G  G  G  S  L  L  A  A  R  D  N  P  S  Y  K  A  A  I  P  M  A  P  W gcaacctcgtccacgccttccgcacggtcagcgtgcccacgatgatcttcggctgtcaggacgacagcatcgccccgtgttcagctct
 A  T  S  S  T  A  F  R  T  V  S  V  P  T  M  I  F  G  C  Q  D  D  S  I  A  P  V  F  S  S gcgatcccgatttacaacgccattccaacagcacgcgcaagaactatgtcgagatccgcaatgacgaccacttatgcgtgatgaacggc
 A  I  P  I  Y  N  A  I  P  N  S  T  R  K  N  Y  V  E  I  R  N  D  D  H  L  C  V  M  N  G ggtgggcatgatgccacgctgggcaagctgggcatctcgtggatgaagcgcttcgtcgacaacgacacgcgctacagcccttcgtctgc
 G  G  H  D  A  T  L  G  K  L  G  I  S  W  M  K  R  F  V  D  N  D  T  R  Y  S  P  F  V  C ggtgcggaatacaaccgcgtggtcagcagctacgaggtctcgcgcttcgtacaacaactgtccgtac      - SEQ ID NO. 7
 G  A  E  Y  N  R  V  V  S  S  Y  E  V  S  R  S  Y  N  N  C  P  Y         - SEQ ID NO. 8
```

FIG. 4

CUTINASE HAVING IMPROVED ENZYMATIC ACTIVITY

CROSS-REFERENCE TO RELATED APPLICATION

This application claims priority to China Patent Application No. 202310105886.5, filed on Feb. 8, 2023, the entire contents of which are incorporated herein by reference for all purposes.

INCORPORATION BY REFERENCE

The Sequence Listing XML having the file name "15258-1717_Sequence_Listing.xml", a creation date of Jun. 21, 2023, and a file size of 11 KB is incorporated herein by reference for all purposes.

FIELD OF THE INVENTION

The present invention relates to a cutinase, and more particularly to a cutinase having improved enzymatic activity.

BACKGROUND OF THE INVENTION

Plastic products have been widely used in many aspects of life due to its high formability and stability and bring many conveniences to human life, but the resulted white pollution has seriously threatened the global ecosystem. At present, the global annual production of synthetic plastics has exceeded 400 million tons, wherein polyethylene terephthalate (PET) is a major contributor to the white pollution. PET is composed of ester bond-linked terephthalic acid (TPA) and ethylene glycol (EG), and is highly stable and difficult to decompose. PET is often used in mineral water bottles, polyester clothes and blister packs, which causes huge amount of waste. Since it takes hundreds of years to completely decompose synthetic plastic waste in natural degrading processes, the plastic waste has been continuously accumulated in the environment and invaded the human food chains. Accordingly, the plastic waste seriously threatens the earth's ecology and the human health, and has become one of the pollution problems of global concern.

The current treatments for PET waste mainly include landfill, incineration, recycling and biodegradation. Although landfill and incineration are the simplest, the generated waste gas and water will cause secondary pollution to the environment. As to recycling, due to the economic efficiency of recycling costs and the performance issues of recycled plastics, the recycling rate remains low at the moment. The biodegradation technology (enzymatic degradation or microbial degradation) can degrade PET into small molecules, which can be further recycled to synthesize PET. Therefore, the biodegradation technology solves the problem of PET waste, and can further recycle the raw materials for PET synthesis. Currently, the biodegradation technology has gradually become a research hotspot due to its environmentally friendly features. The scientists have been looking for effective PET biodegradation methods for a long time, and now they have found PET degradation activities from esterases, lipases and cutinases, proving the possibility of PET biodegradation. For example, TfH and TfH BTA-2 from *Thermobifida fusca*, LC cutinase from leaf compost, and lipase B from *Candida antarctica*, etc., have all been confirmed to have PET degradation activities. However, since PET is not the major reactant of the above-mentioned enzymes, the PET degradation rate is still low, resulting in low industrial application values of the above-mentioned enzymes.

In 2016, a Japanese research team reported magical bacteria named *Ideonella sakaiensis* that can "eat plastic". The bacteria can secrete a new type of PET hydrolase (IsPETase), which is able to decompose PET into small fragments of mono(2-hydroxyethyl) terephthalic acid (MHET) at 30° C., and the decomposed products can be further digested by the bacteria and finally converted into two simple molecules, terephthalic acid (TPA) and ethylene glycol (EG). Although the IsPETase has relatively higher activity in degrading PET than other esterases or cutinases and has potential industrial application value, its degradation efficiency is still low, and there is still a gap from commercial applications. Thus, the scientists have also conducted a lot of subsequent researches, whether by screening new genes from nature or modifying existing enzymes, in order to find PET hydrolases that are more suitable for industrial applications. In many strategies for modifying the enzyme, the protein engineering by rational design based on structural analysis is one of the major strategies for enzyme improvement. The higher enzymatic activity represents the lower cost and the higher profit, which is beneficial to industrial applications.

Therefore, the present invention intends to modify an existing enzyme, so as to improve its PET-hydrolytic activity, thereby increasing its industrial application value.

SUMMARY OF THE INVENTION

An object of the present invention is to modify an existing cutinase by means of structural analysis and site-directed mutagenesis for improving the PET-hydrolytic activity of the cutinase and further increasing its industrial application value.

According to an aspect of the present invention, there is provided a modified cutinase. The cutinase has the modified amino acid sequence of SEQ ID NO: 2, wherein the modification is a substitution of asparagine at position 181 with alanine, or substitutions of asparagine at position 181 with alanine and phenylalanine at position 235 with leucine.

In an embodiment, the cutinase has the full length amino acid sequence of SEQ ID NO: 6.

In an embodiment, the cutinase has the full length amino acid sequence of SEQ ID NO: 8.

According to another aspect of the present invention, there is provided a nucleic acid encoding the aforesaid cutinase, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the CtPL-DM;

FIG. 2 shows the primer sequences for site-directed mutagenesis;

FIG. 3 shows the nucleotide sequence and the amino acid sequence of the mutant CtPL-DM-N181A;

FIG. 4 shows the nucleotide sequence and the amino acid sequence of the mutant CtPL-DM-N181A/F235L;

DETAILED DESCRIPTION OF THE PREFERRED EMBODIMENT

Figure 5:
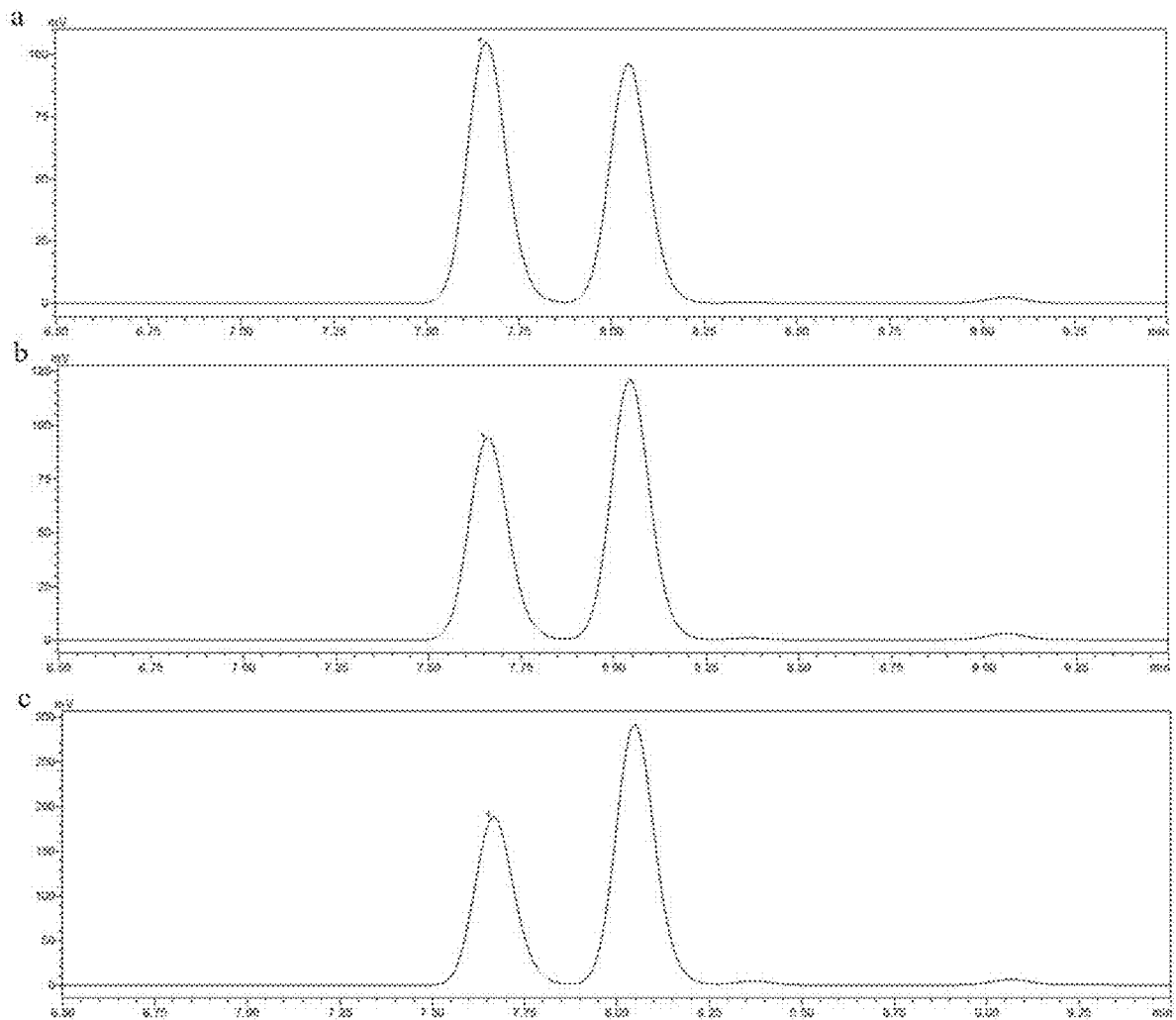
FIG. 5 shows the HPLC analysis of the PET degradation products resulted by the CtPL-DM and the mutants.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The cutinase gene CtPL utilized in the present invention was isolated from *Caldimonas taiwanensis*. This cutinase is an analogous enzyme to the IsPETase, and its protein sequence has 51.0% identity with the IsPETase. Previous studies have shown that the cutinase CtPL also has PET-hydrolytic activity and thus has potential application value. At present, there are few literature reports related to the CtPL, and there are still many unknowns about its enzyme structure and mechanism of degrading PET, which need further researches to clarify. The scientists have also conducted a lot of modifications to increase the activity of the CtPL. Particularly, the research team of the applicant has analyzed the structure of the CtPL and obtained the $CtPL^{H210S/F214I}$ mutant (referred to as CtPL-DM) through rational design and modification to increase its PET-hydrolytic activity. Although the PET-hydrolytic activity of the CtPL-DM has increased, the CtPL-DM has not been produced industrially so far, and there is still a long way from commercial application.

The *Pichia pastoris* expression system has the advantages of low cost, high-density fermentation, high expression of exogenous proteins, external secretion, and capable of post-translational modification, such as glycosylation, phosphorylation and disulfide bonds formation, of exogenous proteins. Thus, the *P. pastoris* expression system is commonly used in industry. The present invention found that the CtPL-DM can be effectively expressed and produced in *P. pastoris*, but its PET-hydrolytic activity is very low. It is speculated that the glycosylation modification during yeast expression may affect the activity of the CtPL-DM. It is also found in other previous studies that although the glycosylation modification can increase the thermal stability of the protein, if the glycosylation site is too close to the active region of the protein, the activity of the protein will also be affected. Therefore, in order to modify the CtPL-DM into a high-activity PET hydrolase, the present invention used X-ray crystallography to further analyze the tertiary structure of the CtPL-DM protein and clarify its detailed structural information, and selected glycosylation sites close to the active region and key sites in the active region for further modification. Based on the structure analysis and comparison, the present invention utilized site-directed mutagenesis to mutate asparagine (N) at position 181 of the CtPL-DM into alanine (A), and mutate phenylalanine (F) at position 235 of the CtPL-DM into leucine (L). The present invention successfully improved the PET-hydrolytic activity of the CtPL-DM, and further increased the industrial application value of the cutinase.

Hereinafter, the enzyme modification method and the resulted PET hydrolase having high enzymatic activity will be described in detail.

First, the CtPL-DM gene was obtained by gene synthesis, and the gene was constructed into pPICZαA vector using EcoRI and NotI restriction enzymes. Then the recombinant plasmid was transformed into a competent cell to obtain the CtPL-DM recombinant plasmid. FIG. 1 shows the nucleotide sequence and the amino acid sequence of the CtPL-DM, wherein the CtPL-DM gene consists of 876 base pairs (SEQ ID NO: 1) and encodes 292 amino acids (SEQ ID NO: 2).

In order to improve the PET-hydrolytic activity of the CtPL-DM, the present invention utilized site-directed mutagenesis by using the CtPL-DM gene as the template and using the mutant primers shown in FIG. 2 to perform the polymerase chain reaction (PCR). The mutant primers include the mutant primer N181A (SEQ ID NO: 3) to mutate asparagine (N) at position 181 into alanine (A) and the mutant primer F235L (SEQ ID NO: 4) to mutate phenylalanine (F) at position 235 into leucine (L). The original template DNA was then removed using DpnI. Subsequently, the mutant plasmid was transformed into *Escherichia coli* competent cells, and the mutant gene was confirmed by DNA sequencing. Here, the present invention constructed two mutant strains of the CtPL-DM, which are CtPL-DM-N181A and CtPL-DM-N181A/F235L. The CtPL-DM-N181A means that asparagine (N) at position 181 of the CtPL-DM is substituted with alanine (A). The CtPL-DM-N181A/F235L means that asparagine (N) at position 181 of the CtPL-DM is substituted with alanine (A) and phenylalanine (F) at position 235 of the CtPL-DM is substituted with leucine (L). FIG. 3 shows the nucleotide sequence and the amino acid sequence of the mutant CtPL-DM-N181A, wherein the CtPL-DM-N181A gene consists of 876 base pairs (SEQ ID NO: 5) and encodes 292 amino acids (SEQ ID NO: 6). FIG. 4 shows the nucleotide sequence and the amino acid sequence of the mutant CtPL-DM-N181A/F235L, wherein the CtPL-DM-N181A/F235L gene consists of 876 base pairs (SEQ ID NO: 7) and encodes 292 amino acids (SEQ ID NO: 8).

The following is to further express and purify the proteins in *P. pastoris*. First, the constructed recombinant plasmids CtPL-DM-N181A and CtPL-DM-N181A/F235L were linearized by PmeI and then transformed into *P. pastoris* by electroporation, respectively. The transformants were selected on YPD plates containing 250 μg/ml zeocin and incubated at 30° C. for 2 days. The selected colonies were inoculated in 5 ml YPD medium at 30° C. for 18 hours, and then amplified in 500 ml BMGY medium at 30° C. to the next day. Then, a total of 0.5% methanol was supplemented every day to induce protein expression. After 4 days of protein induction and expression, the medium was centrifuged at 3500 rpm and the supernatant was collected for the next step of purification. To obtain high-purity enzyme protein, the present invention used nickel ion chromatography column and SP cation exchange column sequentially to purify protein by fast protein liquid chromatography (FPLC). Finally, the purified target protein was concentrated in the buffer containing 25 mM Tris-HCl, pH 8.0 and stored at −80° C.

The PET-hydrolytic activities of the three cutinases were measured to compare the activity difference between the CtPL-DM and the mutants. The method for measuring the PET-hydrolytic activity was as follows. The reaction buffer contained 50 mM glycine, pH 9.0, and each reaction mixture (1 mL) included amorphous PET film (GfPET purchased from Goodfellow with crystallinity of 7.3%) and 10 μL of enzyme (1 mg/mL). After mixing, the reaction tube was incubated in a metal bath of 60° C. with agitation at 800 rpm for 18 hours. Each reaction condition was performed in triplet. The reaction was terminated by heating at 100° C. for 10 min. Then the reaction mixture was centrifuged at 12000 rpm for 10 minutes, and the supernatant was filtered through a 0.22 μm filter membrane. The filtered supernatant in each group was determined and analyzed by HPLC equipped with C18 column (4.6×250 mm, 5 μm). The mobile phase was methanol/phosphate (20 mM, pH 2.5), the flow rate was 1 ml/min, the detection wavelength is 254 nm, the elution condition is 0-15 minutes, and the methanol linear gradient is 35-70%.

Figure 6:
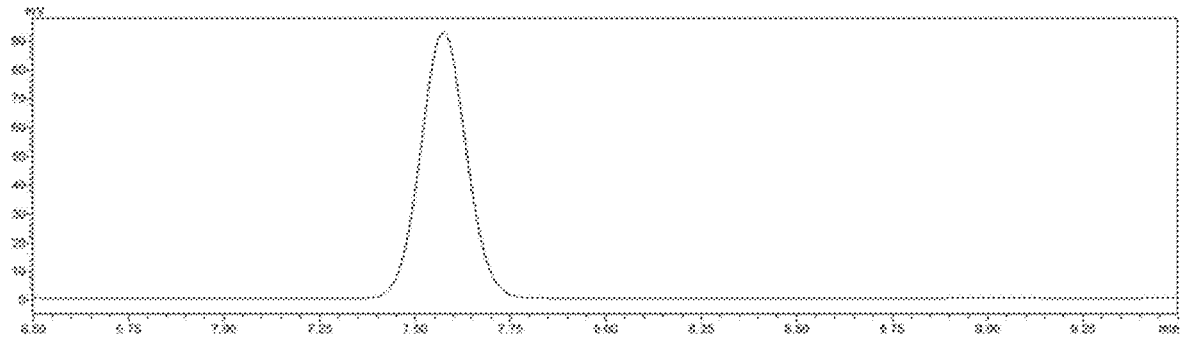
FIG. 6 shows the HPLC analysis of the standard product TPA.
Figure 7:
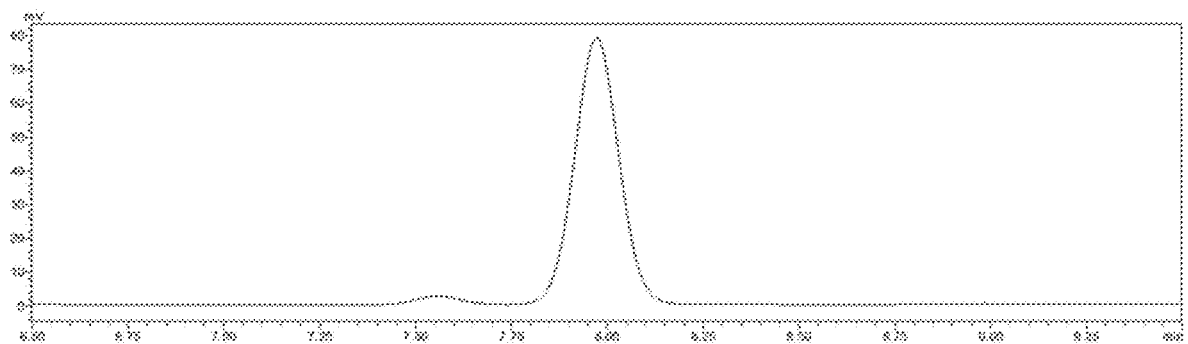
FIG. 7 shows the HPLC analysis of the standard product MHET.

FIG. 5 shows the HPLC analysis of the PET degradation products resulted by the CtPL-DM and the mutants, wherein the subfigure a shows the HPLC analysis for the CtPL-DM, the subfigure b shows the HPLC analysis for the CtPL-DM-N181A, and the subfigure c shows the HPLC analysis for the CtPL-DM-N181A/F235L. As shown in FIG. 5, all detections peaked at a retention time of 7.66 minutes and a retention time of 8.04 minutes. The peak time with a retention time of 7.66 minutes was consistent with the standard product TPA (FIG. 6), so the substance with a retention time of 7.66 minutes was TPA. The peak time with a retention time of 8.04 minutes was consistent with the standard product MHET (FIG. 7), so the substance with a retention time of 8.04 minutes was MHET. Then, the peak areas of the degradation products MHET and TPA of the CtPL-DM, the CtPL-DM-N181A and the CtPL-DM-N181A/F235L were respectively converted into product concentrations via the standard curves of MHET and TPA. The PET-hydrolytic activity was defined as the sum of the concentrations of MHET and TPA.

Figure 8:
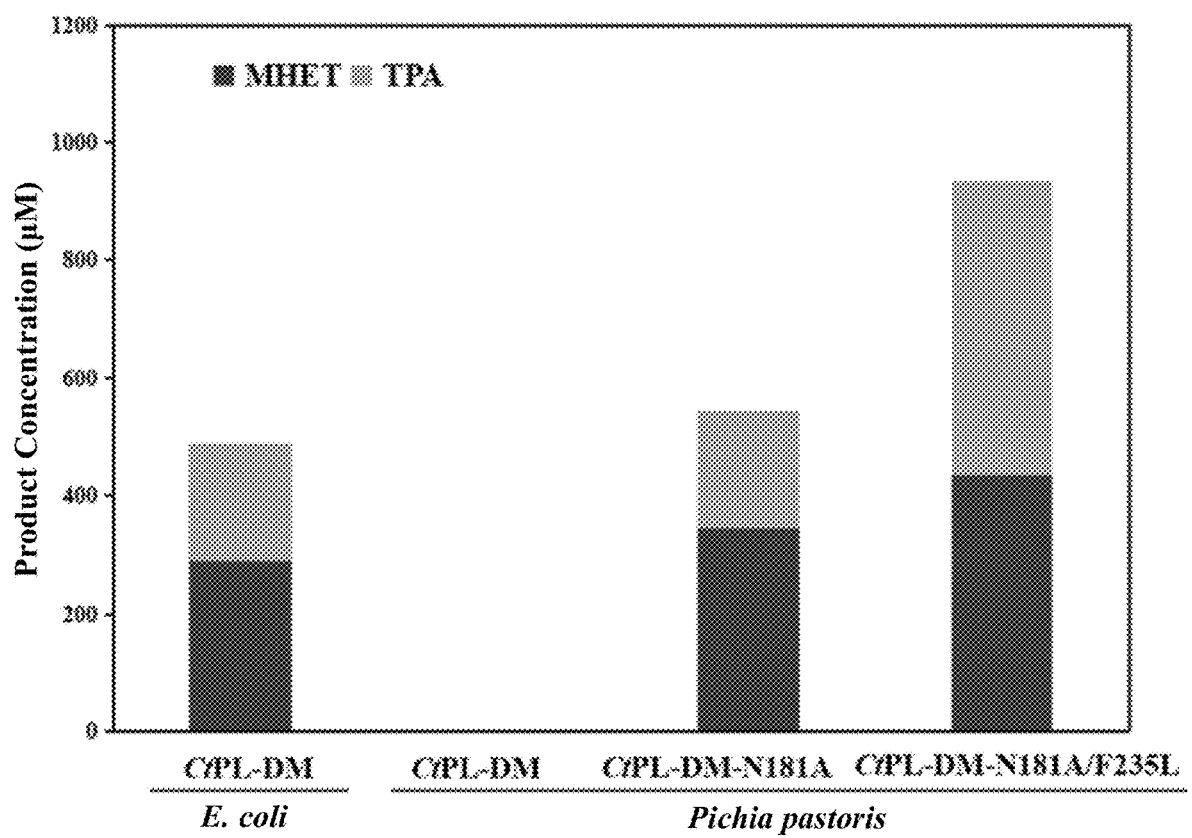
FIG. 8 shows the PET-hydrolytic activity analysis of CtPL-DM and the mutants.

FIG. 8 shows the PET-hydrolytic activity analysis of the CtPL-DM and the mutants. As shown in FIG. 8, the CtPL-DM expressed in *P. pastoris* had extremely low activity, while the mutants CtPL-DM-N181A and CtPL-DM-N181A/F235L had significantly improved activity. Under the reaction condition of 60° C., the PET-hydrolytic activity of the CtPL-DM-N181A expressed in *P. pastoris* was 111% of that of the CtPL-DM expressed in *E. coli*, which means the activity had been restored to a comparable level of the CtPL-DM expressed in *E. coli*. The PET-hydrolytic activity of the CtPL-DM-N181A/F235L expressed in *P. pastoris* was 191% of that of the CtPL-DM expressed in *E. coli* and 171% of that of the CtPL-DM-N181A expressed in *P. pastoris*. Further, the CtPL-DM-N181A and the CtPL-DM-N181A/F235L were also subjected to *P. pastoris* fermentation at 30 L scale to simulate industrial production. According to the 30 L fermentation result, the CtPL-DM-N181A and the CtPL-DM-N181A/F235L also had significantly improved activities, and the activity of the CtPL-DM-N181A/F235L was also significantly higher than that of the CtPL-DM-N181A. Therefore, the present invention significantly increased the PET-hydrolytic activities of the CtPL-DM-N181A and the CtPL-DM-N181A/F235L expressed in *P. pastoris*, which improves their application values in the PET degradation industry. Further, *P. pastoris* is capable of large-scale fermentation, and thus is suitable for high-density cultivation and beneficial for industrial scale-up production of recombinant proteins. Accordingly, the present invention successfully designed the high-yield and high-activity PET hydrolases.

In conclusion, in order to modify the cutinase CtPL-DM into a PET hydrolase having improved PET-hydrolytic activity, the present invention utilized structural analysis and site-directed mutagenesis to modify the CtPL-DM. The modified mutants CtPL-DM-N181A and CtPL-DM-N181A/F235L can be expressed in *P. pastoris*, and the PET-hydrolytic activities thereof are successfully improved. Thus, the high-activity PET hydrolase is obtained, and the industrial application value of the PET hydrolase is enhanced. Besides, the enzymes usually have some variations among different species but still have the same function, and most of them have at least 80%, 85%, 90% or 95% identity in amino acid sequence. Obviously, the enzymes are allowed to have some amino acid sequence variations but still maintain the enzyme function. In other words, the sequence of the modified PET hydrolase provided in the present invention is not limited to SEQ ID NO: 6 or 8, but also includes the sequence with at least 80%, 85%, 90% or 95% sequence identity of SEQ ID NO: 6 or 8 except for mutation sites.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cutinase having the modified amino acid sequence of SEQ ID NO: 2, wherein the modification is a substitution of asparagine at position 181 with alanine, or substitutions of asparagine at position 181 with alanine and phenylalanine at position 235 with leucine.

2. The cutinase according to claim 1 having the full length amino acid sequence of SEQ ID NO: 6.

3. The cutinase according to claim 1 having the full length amino acid sequence of SEQ ID NO: 8.

4. A nucleic acid encoding the cutinase of claim 1.

5. A recombinant plasmid comprising the nucleic acid of claim 4.

* * * * *

SEQUENCE LISTING

```
Sequence total quantity: 8
SEQ ID NO: 1            moltype = DNA   length = 876
FEATURE                 Location/Qualifiers
source                  1..876
                        mol_type = other DNA
                        organism = synthetic construct
SEQUENCE: 1
agcccatcga ccctctcaac aatcctgctg gccgcctgcg ccgcgctggc cgcaccgggc   60
ctggcccagg cgaacccata tcaaaaaggc cccgatccca cggcttcggc cttggaacgc  120
aacgggccgt ttgccatccg cagcacctcg gtgtcgcgca cctcggtcag cggcttcggc  180
ggcggacgcc tgtactatcc gaccgccagc ggcacctacg gcgccatcgc ggtgtcgccc  240
gggttcaccg gcacgtcctc gaccatgacc ttctggggcg agcgcctggc ttcgcacggc  300
ttcgtcgtgc tggtgatcga caccatcacc ttgtacgacc agcccgacag ccgcgcccgt  360
cagctcaagg cagcactgga ctacctggcc acgcagaacg gccgcagcag cagcccgatc  420
taccgcaagg tcgacaccag ccgccgcgcc gtgggccggc attcgatggg cgaggccggc  480
tcgctgctgg ccgcgcgtga caatcccagt tacaaagccg ccatcccgat ggcacccctgg  540
aacacctcgt ccacggcctt ccgcacggtc agcgtgccca cgatgatctt cggctgtcag  600
gacgacagca tcgcccggt gttcagctct gcgatcccga tttacaacgc cattcccaac  660
agcacgcgca agaactatgt cgagatccgc aatgacgacc acttctgcgt gatgaacggc  720
ggtgggcatg atgccacgct gggcaagctg ggcatctcgt ggatgaagcg cttcgtcgac  780
```

```
aacgacacgc gctacagccc cttcgtctgc ggtgcggaat acaaccgcgt ggtcagcagc    840
tacgaggtct cgcgttcgta caacaactgt ccgtac                              876

SEQ ID NO: 2           moltype = AA  length = 292
FEATURE                Location/Qualifiers
source                 1..292
                       mol_type = protein
                       organism = synthetic construct
SEQUENCE: 2
SPSTLSTILL AACAALAAPG LAQANPYQKG PDPTASALER NGPFAIRSTS VSRTSVSGFG     60
GGRLYYPTAS GTYGAIAVSP GFTGTSSTMT FWGERLASHG FVVLVIDTIT LYDQPDSRAR    120
QLKAALDYLA TQNGRSSSPI YRKVDTSRRA VAGHSMGGGG SLLAARDNPS YKAAIPMAPW    180
NTSSTAFRTV SVPTMIFGCQ DDSIAPVFSS AIPIYNAIPN STRKNYVEIR NDDHFCVMNG    240
GGHDATLGKL GISWMKRFVD NDTRYSPFVC GAEYNRVVSS YEVSRSYNNC PY            292

SEQ ID NO: 3           moltype = DNA  length = 40
FEATURE                Location/Qualifiers
source                 1..40
                       mol_type = other DNA
                       organism = synthetic construct
SEQUENCE: 3
cccgatggca ccctgggcaa cctcgtccac ggccttccgc                           40

SEQ ID NO: 4           moltype = DNA  length = 34
FEATURE                Location/Qualifiers
source                 1..34
                       mol_type = other DNA
                       organism = synthetic construct
SEQUENCE: 4
ccgcaatgac gaccacttat gcgtgatgaa cggc                                 34

SEQ ID NO: 5           moltype = DNA  length = 876
FEATURE                Location/Qualifiers
source                 1..876
                       mol_type = other DNA
                       organism = synthetic construct
SEQUENCE: 5
agcccatcga ccctctcaac aatcctgctg gccgcctgcg ccgcgctggc cgcaccgggc     60
ctggcccagg cgaacccata tcaaaaaggc cccgatccca cggcttcggc cttgaacgc    120
aacgggccgt ttgccatccg cagcacctcg gtgtcgcgca cctcggtcag cggcttcggc    180
ggcggacgcc tgtactatcc gaccgccagc ggcacctacg gcgccatcgc ggtgtcgccc    240
gggttcaccg gcacgtcctc gaccatgacc ttctggggcg agcgcctggc ttcgcacggc    300
ttcgtcgtgc tggtgatcga caccatcacc ttgtacgacc agcccgacag ccgcgcccgt    360
cagctcaagg cagcactgga ctacctggcc acgcagaacg gccgcagcag cagcccgatc    420
taccgcaagg tcgacaccag ccgccgcgcc gtggccggcc attcgatggg cggaggcggc    480
tcgctgctgg ccgcgcgtga caatcccagt tacaaagccg ccatcccgat ggcacccctgg    540
gcaacctcgt ccacggcctt ccgcacggtc agcgtgccca cgatgatctt cggctgtcag    600
gacgacagca tcgccccggt gttcagtctc gcgatcccga tttacaacgc cattccccaac    660
agcacgcgca gaactatgt cgagatccgc aatgacgacc acttctgcgt gatgaacggc    720
ggtgggcatg atgccacgct gggcaagctg gcatctcgt ggatgaagcg cttcgtcgac    780
aacgacacgc gctacagccc cttcgtctgc ggtgcggaat acaaccgcgt ggtcagcagc    840
tacgaggtct cgcgttcgta caacaactgt ccgtac                              876

SEQ ID NO: 6           moltype = AA  length = 292
FEATURE                Location/Qualifiers
source                 1..292
                       mol_type = protein
                       organism = synthetic construct
SEQUENCE: 6
SPSTLSTILL AACAALAAPG LAQANPYQKG PDPTASALER NGPFAIRSTS VSRTSVSGFG     60
GGRLYYPTAS GTYGAIAVSP GFTGTSSTMT FWGERLASHG FVVLVIDTIT LYDQPDSRAR    120
QLKAALDYLA TQNGRSSSPI YRKVDTSRRA VAGHSMGGGG SLLAARDNPS YKAAIPMAPW    180
ATSSTAFRTV SVPTMIFGCQ DDSIAPVFSS AIPIYNAIPN STRKNYVEIR NDDHFCVMNG    240
GGHDATLGKL GISWMKRFVD NDTRYSPFVC GAEYNRVVSS YEVSRSYNNC PY            292

SEQ ID NO: 7           moltype = DNA  length = 876
FEATURE                Location/Qualifiers
source                 1..876
                       mol_type = other DNA
                       organism = synthetic construct
SEQUENCE: 7
agcccatcga ccctctcaac aatcctgctg gccgcctgcg ccgcgctggc cgcaccgggc     60
ctggcccagg cgaacccata tcaaaaaggc cccgatccca cggcttcggc cttgaacgc    120
aacgggccgt ttgccatccg cagcacctcg gtgtcgcgca cctcggtcag cggcttcggc    180
ggcggacgcc tgtactatcc gaccgccagc ggcacctacg gcgccatcgc ggtgtcgccc    240
gggttcaccg gcacgtcctc gaccatgacc ttctggggcg agcgcctggc ttcgcacggc    300
ttcgtcgtgc tggtgatcga caccatcacc ttgtacgacc agcccgacag ccgcgcccgt    360
cagctcaagg cagcactgga ctacctggcc acgcagaacg gccgcagcag cagcccgatc    420
taccgcaagg tcgacaccag ccgccgcgcc gtggccggcc attcgatggg cggaggcggc    480
```

```
tcgctgctgg ccgcgcgtga caatcccagt tacaaagccg ccatcccgat ggcaccctgg  540
gcaacctcgt ccacggcctt ccgcacggtc agcgtgccca cgatgatctt cggctgtcag  600
gacgacagca tcgccccggt gttcagctct gcgatcccga tttacaacgc cattcccaac  660
agcacgcgca agaactatgt cgagatccgc aatgacgacc acttatgcgt gatgaacggc  720
ggtgggcatg atgccacgct gggcaagctg ggcatctcgt ggatgaagcg cttcgtcgac  780
aacgacacgc gctacagccc cttcgtctgc ggtgcggaat acaaccgcgt ggtcagcagc  840
tacgaggtct cgcgttcgta caacaactgt ccgtac                            876

SEQ ID NO: 8              moltype = AA   length = 292
FEATURE                   Location/Qualifiers
source                    1..292
                          mol_type = protein
                          organism = synthetic construct
SEQUENCE: 8
SPSTLSTILL AACAALAAPG LAQANPYQKG PDPTASALER NGPFAIRSTS VSRTSVSGFG    60
GGRLYYPTAS GTYGAIAVSP GFTGTSSTMT FWGERLASHG FVVLVIDTIT LYDQPDSRAR   120
QLKAALDYLA TQNGRSSSPI YRKVDTSRRA VAGHSMGGGG SLLAARDNPS YKAAIPMAPW   180
ATSSTAFRTV SVPTMIFGCQ DDSIAPVFSS AIPIYNAIPN STRKNYVEIR NDDHLCVMNG   240
GGHDATLGKL GISWMKRFVD NDTRYSPFVC GAEYNRVVSS YEVSRSYNNC PY           292
```